United States Patent [19]

Bell

[11] 4,349,558
[45] Sep. 14, 1982

[54] ANTI-INFLAMMATORY 8H-PHENANTHRO-[2,3-C]PYRAZOLE DERIVATIVES

[75] Inventor: Malcolm R. Bell, East Greenbush, N.Y.

[73] Assignee: Sterling Drug Inc., New York, N.Y.

[21] Appl. No.: 235,440

[22] Filed: Feb. 19, 1981

[51] Int. Cl.$^3$ .................. A61K 31/415; C07D 231/54
[52] U.S. Cl. ............................... 424/273 P; 548/369
[58] Field of Search .................. 548/369; 424/273 P

[56] References Cited
PUBLICATIONS

Fried et al., J. Am. Chem. Soc. 85, 236–238 (1963).

*Primary Examiner*—Henry R. Jiles
*Assistant Examiner*—Natalia Harkaway
*Attorney, Agent, or Firm*—Thomas L. Johnson; B. Woodrow Wyatt

[57] ABSTRACT

The compounds of the formulas

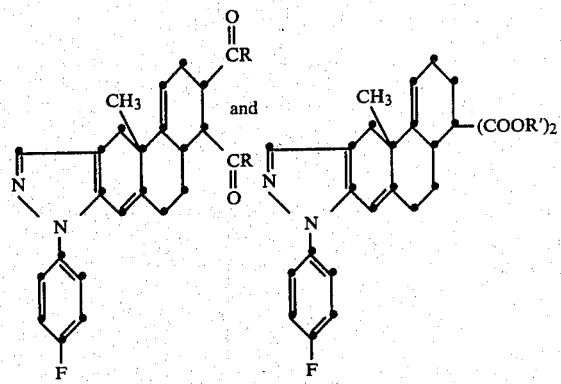

where R and R' are lower-alkyl possess glucocorticoid activity, and are prepared by reacting the compound of the formula

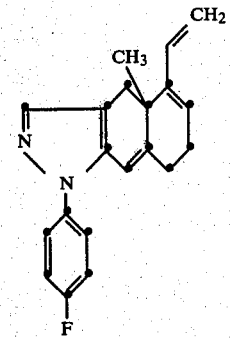

with the appropriate dienophile.

5 Claims, No Drawings

ANTI-INFLAMMATORY 8H-PHENANTHRO-[2,3-C]PYRAZOLE DERIVATIVES

BACKGROUND OF THE INVENTION (1) Field of the Invention

The present invention relates to novel polycyclic fused pyrazole compounds, their use as anti-inflammatory agents, and a method of preparation thereof.

(2) Description of the Prior Art

Typical glucocorticoid activity is rarely found in structures which do not possess an intact steroid nucleus. Such activity is found in naturally occurring steroids such as cortisone, hydrocortisone and aldosterone, as well as numerous synthetic modifications thereof, all containing the intact steroid nucleus. An example of a synthetic cortical steroid having high activity is a fluorophenylpyrazole derivative reported by Fried et al., J. Am. Chem. Soc. 85, 236 (1963), having the structure

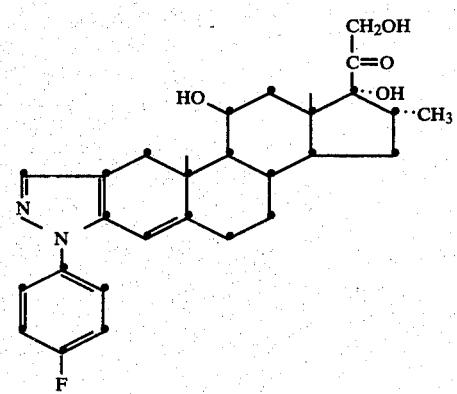

SUMMARY OF THE INVENTION

In a product aspect, the invention relates to compounds having the formulas:

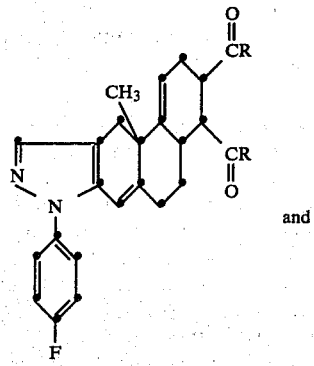

I

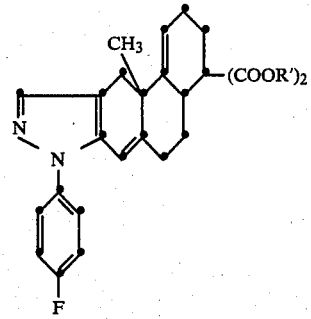

II wherein R and R' are lower-alkyl groups.

In a further product aspect, the invention relates to a pharmaceutical composition for treating inflammation in mammals which comprises an anti-inflammatorily effective amount of a compound of formula I or II and a pharmaceutically acceptable carrier.

In a still further product aspect, the invention relates to an intermediate in the preparation of the compounds of formulas I and II, said intermediate having the formula:

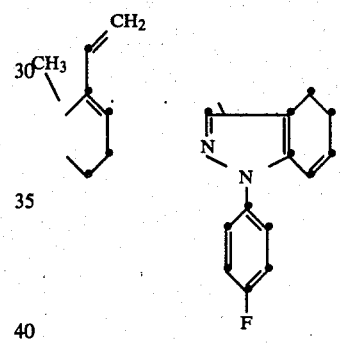

III

In a process aspect, the invention relates to a process for preparing the compounds of formulas I or II by reacting the compound of formula III with a compound of the formula RCOCH=CHCOR or CH$_2$=C(COOR')$_2$, respectively.

In a further process aspect, the invention relates to a method of reducing inflammation in a mammal which comprises administering to said mammal an anti-inflammatorily effective amount of a compound of formula I or II.

DETAILED DESCRIPTION INCLUSIVE OF PREFERRED EMBODIMENTS

The novel intermediate of formula III is prepared from a known starting material, 5-ethenyl-4,4a,7,8-tetrahydro-4a-methyl-2(3H)-naphthalenone (cf. Bell et al. U.S. Pat. No. 4,157,349, June 5, 1979) in accordance with the following reactions:

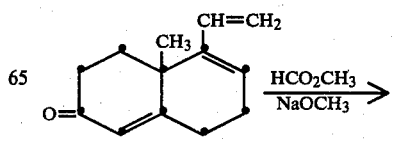

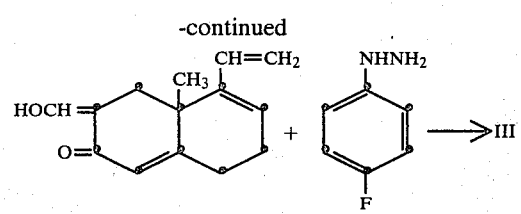

The trienone starting material is reacted with methyl formate in the presence of sodium methoxide in an inert solvent such as tetrahydrofuran to afford 5-ethenyl-3-hydroxymethylene-4,4a,7,8-tetrahydro-4a-methyl-2(3H)-naphthalenone, and the latter is then reacted with 4-fluorophenylhydrazine or an acid-addition salt thereof in the presence of acetic acid to give the compound of formula III.

A compound of formula I is prepared by reacting the compound of formula III with an unsaturated diketone of the formula RCOCH=CHCOR. The reaction takes place by heating the reactants in an inert solvent at a temperature between about 50° and 150° C. Similarly, a compound of formula II is prepared by heating III with a di-lower-alkyl methylenemalonate [$CH_2$=C(COOR')$_2$]. In order to suppress the tendency of the diene to polymerize, a small quantity of a free radical chain reaction inhibitor such as 1,2,3-benzenetriol (pyrogallol), may be added.

The lower-alkyl groups R and R' preferably have from one to four carbon atoms, including, for example, methyl, ethyl, propyl, isopropyl, butyl and isobutyl.

The compounds of formulas I and II exhibit an endocrinological profile characteristic of compounds possessing glucocorticoid properties and systemic and/or topical anti-inflammatory activity; cf. R. H. Silber, The Biology of Anti-inflammatory Steroids, Annals of the New York Academy of Sciences, Vol. 82, Art. 4, pp. 821–828.

When the compounds of formulas I and II are administered orally to rats they cause a significant depression in thymus weight, adrenal weight and body weight gain without a change in food consumption.

The compound of formula I where R is methyl has also been found to possess oral glucocorticoid activity by the liver glycogen deposition test and anti-inflammatory activity by the α-tocopherol pouch test in rats.

The test procedures used to determine the biological activities of the compounds of the invention were carried out as follows:

Endocrine Profile:

Mature female rats with an average body weight of 202 g and a body weight range of 15 g or less were medicated orally with test compound for 2 weeks. The test compound was prepared as a solution or suspension in 1% gum tragacanth or 0.75% methyl cellulose. On the day following the last medication, the rats were killed and the thymus and adrenal of each rat were removed, cleaned, and weighed. Body weights and food consumptions were also recorded.

Anti-inflammatory Activity (α-tocopherol pouch test):

Male rats which weighed 120 g were selected for testing. A rapid subcutaneous injection of 25 mL of air was made between the scapulae of each rat. This resulted in the establishment of an airfilled pouch into which 0.5 mL of dl-α-tocopherol was injected. The test compound was administered in daily oral doses for 7 days beginning on the day of pouch formation. The compound to be tested was suspended in 1% gum tragacanth. Twenty-four hours after the last medication, the pouches were dissected free, and the fluid volume was measured. The inhibition of liquid exudate is a measure of the anti-inflammatory activity.

Glycogenic Activity:

Mature male rats were bilaterally adrenalectomized 5 days prior to the test. These rats were medicated orally with the test compound for 5 days. Seven hours after the last medication, the rats (which have been fasted overnight) were anesthetized with sodium pentobarbital and a portion of one lobe of the liver was removed and frozen on dry ice for subsequent glycogen determination.

The compounds of the invention can be formulated for topical application by solution or dispersion in a conventional pharmaceutically acceptable liquid, cream or ointment base. The effective ingredient is preferably present in a concentration of 0.01% to 5.0% by weight.

The compounds of the invention can be formulated for oral administration in tablet or capsule form with conventional excipients. The active ingredient is preferably present in an amount of 1 mg to 100 mg per unit dosage form.

The following examples will further illustrate the invention.

EXAMPLE 1

(a)

5-Ethenyl-3-hydroxymethylene-4,4a,7,8-tetrahydro-4a-methyl-2(3H)-naphthalenone

A solution of 50.0 g (0.265 mol) of 5-ethenyl-4,4a,7,8-tetrahydro-4a-methyl-2(3H)-naphthalenone in 350 mL of tetrahydrofuran was cooled to −5° C. in an ice-methanol bath and stirred under nitrogen while 57.2 g (1.06 mol) of sodium methoxide was added. The resulting mixture was stirred for 30 min at −5° C. and then a solution of 114 mL (1.85 mol) of methyl formate in 100 mL of tetrahydrofuran was added slowly. The mixture was stirred overnight at room temperature and then poured onto a mixture of ice-water (1500 mL) and 6 N hydrochloric acid (265 mL). The product was extracted with ether and the combined extracts were washed with water. The dried extract was dried over anhydrous magnesium sulfate and concentrated in vacuo to afford an oil. This oil was triturated with hexane (4×250 mL) and the combined triturates were dried over magnesium sulfate and concentrated in vacuo to afford 55.37 g of a red oil, consisting essentially of the above-entitled compound as established by proton NMR (PMR) spectral data.

(b)

1-Ethenyl-6-(4-fluorophenyl)-3,4,9,9a-tetrahydro-9a-methyl-6H-naphtho[2,3-c]pyrazole (III)

4-Fluorophenylhydrazine hydrochloride (45.85 g, 0.282 mol) and sodium acetate (23.14 g, 0.282 mol) were added to a solution of 55.37 g (0.256 mol) of the product obtained in part (a) above in 225 mL of glacial acetic acid. The mixture was stirred overnight at room temperature and then concentrated in vacuo to afford a semi-solid. This material was suspended in ether (1 L) and filtered to remove sodium chloride. The ether filtrate was washed with water (4×250 mL), saturated sodium bicarbonate (until weakly basic) and saturated sodium chloride (100 mL). The extract was dried over anhydrous magnesium sulfate, decolorized with charcoal and concentrated in vacuo to afford an oil. This oil was triturated with 1:2 ether-hexane (3×750 mL) to afford 69.58 g of a dark brown oil. An analytical sample was prepared by using high-performance liquid chromatography with 1:3 ether-hexane as solvent. The resulting yellow oil was triturated with pentane to afford 1-ethenyl-6-(4-fluorophenyl)-3,4,9,9a-tetrahydro-9a-methyl-6H-naphtho[2,3-c]pyrazole as a yellow solid, m.p. 70°–72° C., with a consistent PMR spectrum.

EXAMPLE 2

1,1'-[8-(4-Fluorophenyl)-2,3,4,4a,5,6,11,11a-octahydro-11a-methyl-8H-phenanthro[2,3-c]pyrazole-3,4-diyl]bis[ethanone] (I; R=CH$_3$)

A solution of 20 g (0.065 mol) of 1-ethenyl-6-(4-fluorophenyl)-3,4,9,9a-tetrahydro-9a-methyl-6H-naphtho[2,3-c]pyrazole in 200 mL benzene and 8.07 g (0.072 mol) of 3-hexene-2,5-dione was stirred at reflux for 40 hours under nitrogen. The cooled reaction mixture was filtered through silica gel and concentrated in vacuo. The resultant oil was triturated with ether to afford 7.54 g of a gold solid as a mixture of isomers, m.p. 138°–142° C., as determined by PMR spectroscopy. Five g of this mixture of isomers was separated using high-performance liquid chromatography with 1:4 ethyl acetate-hexane. The major isomer was recrystallized from CH$_2$Cl$_2$-isooctane to afford 3.0 g of 1,1'-[8-(4-fluorophenyl)-2,3,4,4a,5,6,11,11a-octahydro-11a-methyl-8H-phenanthro[2,3-c]pyrazole-3,4-diyl]bis[ethanone], a white solid, m.p. 157°–159° C., a single isomer as determined by PMR spectroscopy.

In the endocrine profile determination, Compound I (R=CH$_3$) at a dose level of 5 mg/kg caused a 59% reduction in weight of the thymus, 40% reduction in adrenal weight and 80% reduction in body weight gain as compared with the controls. In the α-tocopherol pouch test, Compound I (R=CH$_3$) was active with ED$_{50}$=23 mg/kg. In the glycogenic activity test, Compound I (R=CH$_3$) at dose levels of 9 and 27 mg/kg/day×5 produced liver glycogen deposition values of 9.42±0.65 and 25.48±3.39 mg/g of tissue, respectively, as compared to 1.75±0.04 mg/g for the vehicle (ethanol-cottonseed oil 1:9 v/v) alone.

By replacing the 3-hexene-2,5-dione in the procedure of Example 2 by a molar equivalent amount of 4-octene-3,6-dione, 5-decene-4,7-dione or 6-dodecene-5,8-dione, it is contemplated that there can be obtained 1,1'-[8-(4-fluorophenyl)-2,3,4,4a,5,6,11,11a-octahydro-11a-methyl-8H-phenanthro[2,3-c]pyrazole-3,4-diyl]bis[propanone] (I; R=CH$_2$CH$_3$), 1,1'-[8-(4-fluorophenyl)-2,3,4,4a,5,6,11,11a-octahydro-11a-methyl-8H-phenanthro[2,3-c]pyrazole-3,4-diyl]bis[butanone] (I; R=CH$_2$CH$_2$CH$_3$), or 1,1'-[8-(4-fluorophenyl)-2,3,4,4a,5,6,11,11a-octahydro-11a-methyl-8H-phenanthro[2,3-c]pyrazole-3,4-diyl]bis[pentanone] (I; R=CH$_2$CH$_2$CH$_2$CH$_3$), respectively.

EXAMPLE 3

Diethyl 8-(4-fluorophenyl)-2,3,4,4a,5,6,11,11a-octahydro-11a-methyl-8H-phenanthro[2,3-c]pyrazole-4,4-dicarboxylate (II; R=CH$_2$CH$_3$)

A solution of 25.81 g (0.084 mol) of 1-ethenyl-6-(4-fluorophenyl)-3,4,9,9a-tetrahydro-9a-methyl-6H-naphtho[2,3-c]pyrazole, 18.1 g (0.105 mol) of diethyl methylenemalonate and 500 mg of 1,2,3-benzenetriol in 200 mL of xylene was refluxed for 20 hours. The cooled reaction mixture was filtered through silica gel and concentrated in vacuo to afford 41.93 g of a brown oil. The oil was purified by using high-performance liquid chromatography with 3:97 ethyl acetate-CH$_2$Cl$_2$ followed by recrystallization from methanol to afford 10.98 g of diethyl 8-(4-fluorophenyl)-2,3,4,4a,5,6,11,11a-octahydro-11a-methyl-8H-phenanthro[2,3-c]pyrazole-4,4-dicarboxylate as a colorless solid, m.p. 133°–135° C. The PMR spectrum was consistent with the assigned structure.

In the endocrine profile determination, Compound II (R=CH$_2$CH$_3$) at a dose level of 100 mg/kg caused an 80% reduction in thymus weight, 47% reduction in adrenal weight and 186% reduction in body weight gain as compared with the controls. Compound II (R=CH$_2$CH$_3$) was inactive in the α-tocopherol pouch test at 100 mg/kg.

By replacing the diethyl methylenemalonate in the procedure of Example 3 by a molar equivalent amount of dimethyl methylenemalonate, dipropyl methylenemalonate or dibutyl methylenemalonate, it is contemplated that there can be obtained dimethyl 8-(4-fluorophenyl)-2,3,4,4a,5,6,11,11a-octahydro-11a-methyl-8H-phenanthro[2,3-c]pyrazole-4,4-dicarboxylate (II; R=CH$_3$), dipropyl 8-(4-fluorophenyl)-2,3,4,4a,5,6,11,11a-octahydro-11a-methyl-8H-phenanthro[2,3-c]pyrazole-4,4-dicarboxylate (II; R=CH$_2$CH$_2$CH$_3$), or dibutyl 8-(4-fluorophenyl)-2,3,4,4a,5,6,11,11a-octahydro-11a-methyl-8H-phenanthro[2,3-c]pyrazole-4,4-dicarboxylate (II; R=CH$_2$CH$_2$CH$_2$CH$_3$), respectively.

I claim:

1. A compound selected from the group consisting of those having the formulas

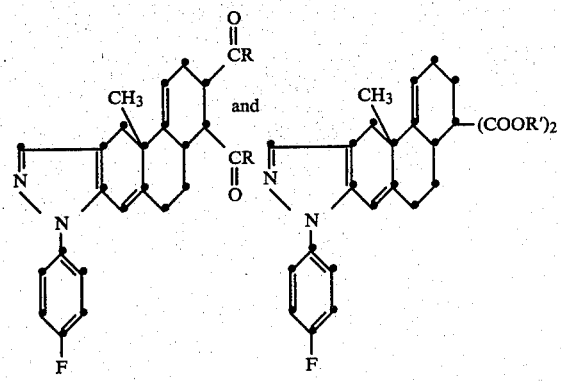

wherein R and R' are lower-alkyl.

2. 1,1'-[8-(4-Fluorophenyl)-2,3,4,4a,5,6,11,11a-octahydro-11a-methyl-8H-phenanthro[2,3-c]pyrazole-3,4-diyl]bis[ethanone], according to claim 1.

3. Diethyl 8-(4-fluorophenyl)-2,3,4,4a,5,6,11,11a-octahydro-11a-methyl-8H-phenanthro[2,3-c]pyrazole-4,4-dicarboxylate, according to claim 1.

4. A pharmaceutical composition for treating inflammation in mammals which comprises an anti-inflammatorily effective amount of a compound according to claim 1 and a pharmaceutically acceptable carrier.

5. A method of reducing inflammation in a mammal which comprises administering to said mammal an anti-inflammatorily effective amount of a compound according to claim 1.

* * * * *

UNITED STATES PATENT AND TRADEMARK OFFICE
CERTIFICATE OF CORRECTION

PATENT NO. : 4,349,558
DATED : September 14, 1982
INVENTOR(S) : Malcolm R. Bell

It is certified that error appears in the above-identified patent and that said Letters Patent are hereby corrected as shown below:

Column 2, formula III should read:

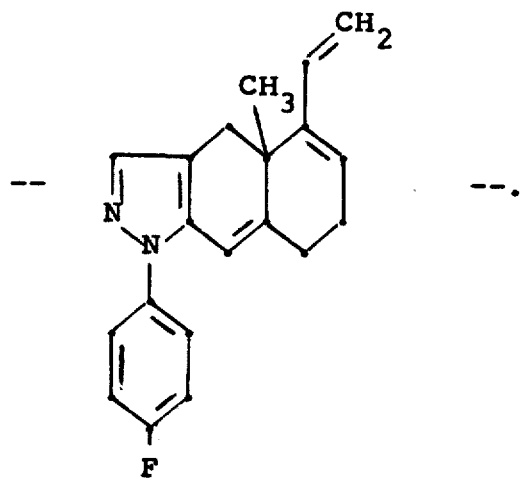

Signed and Sealed this

First Day of February 1983

[SEAL]

Attest:

GERALD J. MOSSINGHOFF

Attesting Officer

Commissioner of Patents and Trademarks